(12) United States Patent
Davis et al.

(10) Patent No.: US 10,179,776 B2
(45) Date of Patent: Jan. 15, 2019

(54) COMPOUNDS AND METHODS OF USE TO TREAT SCHIZOPHRENIA

(71) Applicant: INTRA-CELLULAR THERAPIES, INC., New York, NY (US)

(72) Inventors: Robert Davis, San Diego, CA (US); Peng Li, New Milford, NJ (US)

(73) Assignee: INTRA-CELLULAR THERAPIES, INC., New York, NY (US)

(*) Notice: Subject to any disclaimer, the term of this patent is extended or adjusted under 35 U.S.C. 154(b) by 0 days.

(21) Appl. No.: 15/317,876

(22) PCT Filed: Jun. 9, 2015

(86) PCT No.: PCT/US2015/034863
§ 371 (c)(1),
(2) Date: Dec. 9, 2016

(87) PCT Pub. No.: WO2015/191554
PCT Pub. Date: Dec. 17, 2015

(65) Prior Publication Data
US 2017/0114037 A1  Apr. 27, 2017

Related U.S. Application Data

(60) Provisional application No. 62/009,849, filed on Jun. 9, 2014.

(51) Int. Cl.
*C07D 401/06* (2006.01)
*A61K 45/06* (2006.01)
*A61K 31/454* (2006.01)

(52) U.S. Cl.
CPC .......... *C07D 401/06* (2013.01); *A61K 31/454* (2013.01); *A61K 45/06* (2013.01); *C07B 2200/05* (2013.01)

(58) Field of Classification Search
CPC ..... C07D 401/06; A61K 45/06; A61K 31/454

USPC ..................................................... 514/211.15
See application file for complete search history.

(56) References Cited

U.S. PATENT DOCUMENTS

| 4,389,330 A | 6/1983 | Tice et al. |
| 4,530,840 A | 7/1985 | Tice et al. |
| 5,538,739 A | 7/1996 | Bodmer et al. |
| 7,166,617 B2 * | 1/2007 | Yamabe ............... C07D 401/06 514/323 |
| 9,393,192 B2 | 7/2016 | Yam et al. |
| 2008/0069885 A1 | 3/2008 | Mesens et al. |
| 2013/0274289 A1 | 10/2013 | Luthringer et al. |
| 2013/0274290 A1 | 10/2013 | Luthringer et al. |

FOREIGN PATENT DOCUMENTS

| EP | 0058481 | 8/1982 |
| GB | 2145422 | 3/1985 |
| WO | WO 1993/022309 | 11/1993 |
| WO | WO 2000/035419 | 6/2000 |
| WO | WO 2004/010981 | 2/2004 |
| WO | WO 2008/112280 | 9/2008 |
| WO | WO 2011/133224 | 10/2011 |
| WO | WO 2012/012524 | 1/2012 |
| WO | WO 2013/155505 | 10/2013 |

OTHER PUBLICATIONS

Olanzapine (Zyprexa) prescription information (1996).*
International Search Report of International PCT/US2015/034863 dated Aug. 21, 2015, 3 pages.

* cited by examiner

*Primary Examiner* — Yong L Chu
(74) *Attorney, Agent, or Firm* — Hoxie & Associates LLC

(57) ABSTRACT

The invention relates to particular 2-((1-(2-hydroxy-2-phenylethyl)piperidin-4-yl)methyl)isoindolin-1-one analogs and pro-drugs, in free, pharmaceutically acceptable salt and/or substantially pure form as described herein, pharmaceutical compositions thereof, and methods of use in the treatment of diseases that can be therapeutically and/or preventively treated by the nerve control function of sigma ligands.

24 Claims, No Drawings

COMPOUNDS AND METHODS OF USE TO TREAT SCHIZOPHRENIA

CROSS-REFERENCE TO RELATED APPLICATIONS

This application is a U.S. National Stage application under 35 U.S.C. 371 claiming benefit of PCT/US2015/034863, filed on Jun. 9, 2015, which claims priority to and the benefit of U.S. Provisional Application Ser. No. 62/009,849 filed Jun. 9, 2014, the contents of each of which are hereby incorporated by reference in their entireties.

FIELD OF THE INVENTION

The invention relates to particular 2-((1-(2-hydroxy-2-phenylethyl)piperidin-4-yl)methyl)isoindolin-1-ones and their analogs, in free, pharmaceutically acceptable salt and/or substantially pure form as described herein, pharmaceutical compositions thereof, and methods of use in the treatment of diseases that can be therapeutically and/or preventively treated by the nerve control function of sigma receptor ligands.

BACKGROUND OF THE INVENTION

The mental disorder schizophrenia dramatically affects the health and well-being of individuals suffering from it. Individuals with schizophrenia can suffer from a myriad of symptoms and may require significant custodial care and continuous drug and/or behavior therapy, leading to substantial social and economic costs, even in the absence of hospitalization or institutionalization.

The symptoms of schizophrenia are divided into three broad classes: positive symptoms, negative symptoms and cognitive dysfunction.

Positive symptoms generally involve the experience of something in consciousness that should not normally be present. For example, hallucinations and delusions represent perceptions or beliefs that should not normally be experienced. In addition to hallucinations and delusions, patients with schizophrenia frequently have marked disturbances in the logical process of their thoughts. Specifically, psychotic thought processes are characteristically loose, disorganized, illogical, or bizarre. These disturbances in thought process frequently produce observable patterns of behavior that are also disorganized and bizarre. The severe disturbances of thought content and process that comprise the positive symptoms often are the most recognizable and striking features of schizophrenia.

In addition to positive symptoms, patients with schizophrenia have been noted to exhibit major deficits in motivation and spontaneity. These symptoms are referred to as negative symptoms.

While positive symptoms represent the presence of something not normally experienced, negative symptoms reflect the absence of thoughts and behaviors that would otherwise be expected and thus reflect a decrease or loss of normal function or the loss or absence of normal behaviors. Negative symptoms of schizophrenia include, for example, flat or blunted affect, lack of concrete thoughts, anhedonia, poor motivation, loss of spontaneity, and loss of initiative. Inflexibility or rigidity of thought represents impairment in the ability to think abstractly. Blunting of affect refers to a general reduction in the ability to express emotion. Motivational failure and inability to initiate activities represent an important source of long-term disability in schizophrenia. Anhedonia reflects a deficit in the ability to experience pleasure and to react appropriately to pleasurable situations.

Positive symptoms such as hallucinations are responsible for much of the acute distress associated with schizophrenia. Negative symptoms appear to be responsible for much of the chronic and long-term disability associated with the disorder. Current treatments for schizophrenia have shown limited benefit in the treatment of negative symptoms.

Negative symptoms of schizophrenia can be further subdivided into primary and secondary negative symptoms. Primary negative symptoms exclude symptoms that are better accounted for by medication side-effects, post-psychotic depression or demoralization. Rather, examples of primary negative symptoms include: affective flattening (for example emotional immobility, unresponsiveness, poor eye contact, and limited body movement); alogia (where the patient exhibits poverty of speech and usually manifests itself by the patient making brief replies during conversation), avolition (the inability to initiate and persist in goal-directed activities), anhedonia, dysphoric mood (depression, anxiety and anger), disturbances in sleep pattern (sleeping during the day, restlessness/night-time activity), abnormal psychomotor activity (pacing, rocking, apathetic immobility), and lack of insight.

Secondary negative symptoms, some of which occur in association with positive symptoms and/or medication side-effects, include for example, movement disorders such as extrapyramidal symptoms, akathisia, tardive dyskinesia and demoralization.

In addition to positive and negative symptoms, patients with schizophrenia also suffer from general symptoms. General symptoms of schizophrenia include, but are not limited to, somatic concern (e.g., physical complaints or beliefs about bodily illness or malfunctions), anxiety, feelings of guilt, tension (e.g., overt physical manifestations of fear, anxiety, and agitation, such as stiffness, tremor, profuse sweating, and restlessness), mannerisms and posturing (e.g., unnatural movements or posture as characterized by an awkward, stilted, disorganized, or bizarre appearance), depression, motor retardation (e.g., reduction in motor activity as reflected in slowing or lessening of movements and speech, diminished responsiveness to stimuli, and reduced body tone), uncooperativeness, unusual thought content (ranging from those which are remote or atypical to those which are distorted, illogical, and patently absurd), disorientation, poor attention, lack of judgment and insight, disturbance of volition, poor impulse control, preoccupation, and active social avoidance. Other general symptoms and examples thereof can be found.

There remains a need to identify medicaments and methods for use in the treatment of negative symptoms of schizophrenia, and furthermore, compositions and methods of treatment which improve on the efficacy of existing therapies.

The sigma receptor/binding sites of the brain are important targets for the development of antipsychotic drugs that are free from the side effects of traditional antipsychotic drugs, or have reduced side effects compared to traditional antipsychotic drugs which have antagonistic activity on the dopamine D2 receptor.

The sigma 1 receptor binding site has been characterized as having high affinity for haloperidol, di-o-tolylguanidine (DTG) and (+)-benzomorphanes such as (+)-pentazocine. The sigma 2 receptor binding site has been characterized as having high affinity for haloperidol and DTG, but low affinity for (+)-benzomorphane.

The sigma 2 receptor binding site in brain exists in the hypothalamus, cerebellum, pons medulla and medulla oblongata. In the hippocampus, frontal lobe and occipital lobe of rat brains, it exists more abundantly than the sigma 1 binding site. It is believed that the sigma 2 binding site is involved in motility functions, especially dystonia.

U.S. Pat. No. 7,166,617, incorporated herein by reference in its entirety, discloses cyclic amide ketone derivatives having high affinity for the sigma receptor, along with some affinity at the 5-HT$_{2A}$ receptor, but without any dopamine receptor binding properties. Certain compounds disclosed in that patent also have high affinity for the sigma ligand binding site and low inhibition constant $K_i$ for sigma 1 and/or sigma 2 (high potency), as well as selective binding profiles completely different from those of conventional known compounds. Such compounds may be useful for treatment of diseases that can be therapeutically and/or preventively treated by the nerve control function of the sigma ligands. Such diseases include, for example, diseases of the central nervous system, gastrointestinal tract, and cardiovascular system. There are potential applications to neurodegenerative disorders, pain, drug addiction and cancer. However, the properties and characteristics of specific derivatives were not disclosed in U.S. Pat. No. 7,166,617 ("the '617 patent").

PCT application PCT/US2011/044697 (WO 2012/012524), incorporated herein by reference in its entirety, discloses methods of treating schizophrenia utilizing the ketone derivatives of the '617 patent. The derivatives are shown to be useful to treat one or more negative symptoms of schizophrenia. The application therefore provides methods and compositions for treating various aspects of schizophrenia. In particular, the application discloses the results of human trials in schizophrenics that demonstrate immediate and sustained improvements in negative symptoms and cognitive functions, and some improvement in positive symptoms. Improvements in mood, anxiety and sleep were particularly noted.

SUMMARY OF THE INVENTION

The present invention discloses compounds of Formula I, which are further derivatives of the '617 patent, particularly derivatives of 2-((1-(2-hydroxy-2-phenylethyl)piperidin-4-yl)methyl)isoindolin-1-one and the following compound:

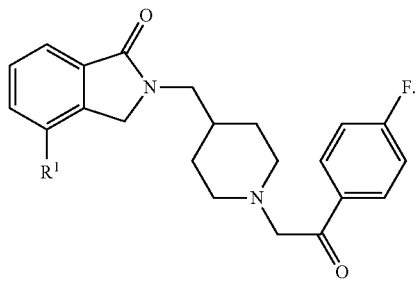

Formula II

Without being bound by any particular theory, it is believed that the ketone functional group of the compound of Formula II converts in vivo to the hydroxy derivative. The compound of the current invention, as defined in Formula I, below seeks to partially or fully block the conversion of this hydroxy back to the ketone by the presence of the $R^2$ or $R^3$ substituent defined below. These compounds are expected to be effective for the treatment of schizophrenia, and other disorders that can be treated by the nerve control function of sigma ligands, while displaying improved drug-like properties compared to the corresponding ketones. In addition, in some embodiments, Compounds of Formula I are pro-drugs that generate the hydroxy derivative in vivo, and by their generation of the hydroxy compound these compounds are expected to be similarly effective for treatment of the diseases and disorders described herein.

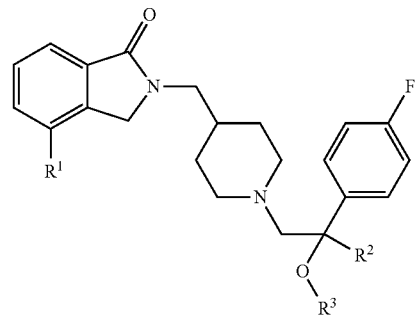

Formula I

Therefore, in the first aspect, the invention provides a compound of Formula I:

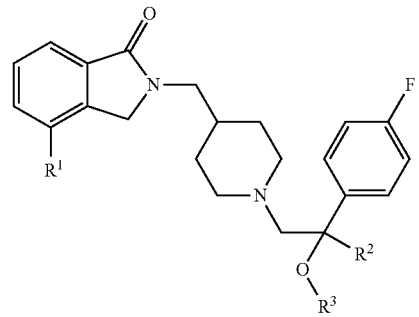

Formula I wherein:
$R^1$ is H or F;
$R^2$ is H, D, F, or $C_{1-6}$ alkyl (e.g., methyl, ethyl or isopropyl);
$R^3$ is H, $C_{1-6}$ alkyl, or a pharmaceutically acceptable and physiologically labile moiety, e.g. a pharmaceutically acceptable and physiologically labile acyl moiety, for example, wherein the labile moiety is —C(O)—$R^4$, and $R^4$ is a $C_{1-21}$ alkyl, e.g., a linear $C_{1-21}$ alkyl,
provided that when $R^2$ is H, $R^3$ is not H, and
further provided that when $R^2$ is H, $R^3$ is not —C(O)—$R^4$ wherein $R^4$ is methyl;
in free form or in the form of a pharmaceutically acceptable salt.

In a further embodiment, the invention provides the compound of Formula I in free or salt form, as described in the following formulae:
1.1. The compound of Formula I, wherein $R^1$ is F;
1.2. The compound of Formula I, wherein $R^1$ is H;
1.3. The compound of Formula I, 1.1 or 1.2, wherein $R^2$ is H;
1.4. The compound of Formula I, 1.1 or 1.2, wherein $R^2$ is D;

1.5. The compound of Formula I, 1.1 or 1.2 wherein $R^2$ is $C_{1-6}$ alkyl (e.g., methyl);
1.6. The compound of Formula I or any of Formulas 1.1 to 1.5, wherein $R^3$ is $C_{1-6}$ alkyl;
1.7. The compound of Formula I or any of Formulas 1.1 to 1.6, wherein $R^3$ is methyl;
1.8. The compound of Formula I or any of Formula 1.1-1.5, wherein $R^3$ is a pharmaceutically acceptable and physiologically labile moiety, e.g. a pharmaceutically acceptable and physiologically labile acyl moiety;
1.9. The compound of Formula I or any of Formula 1.1-1.5 or 1.8, wherein $R^3$ is —C(O)—$R^4$, and wherein $R^4$ is $C_{1-21}$ alkyl;
1.10. The compound of Formula I or any of Formula 1.1-1.5 or 1.8-1.9, wherein $R^3$ is —C(O)—$R^4$, and wherein $R^4$ is $C_{1-15}$ alkyl;
1.11. The compound of Formula I or any of Formula 1.1-1.5 or 1.8-1.10, wherein $R^3$ is —C(O)—$R^4$, and wherein $R^4$ is $C_{1-9}$ alkyl
1.12. The compound of Formula I or any of Formula 1.1-1.5 or 1.8-1.11, wherein $R^3$ is —C(O)—$R^4$, and wherein $R^4$ is methyl, ethyl or propyl;
1.13. The compound of Formula I or any of Formula 1.1-1.5 or 1.8-1.12, wherein $R^3$ is —C(O)—$R^4$, and wherein $R^4$ is methyl;
1.14. The compound of Formula I or any of Formula 1.1-1.5, wherein $R^3$ is H;
1.15. The compound of Formula I or any of Formula 1.1-1.14, wherein the salt is a hydrochloric acid salt;
1.16. The compound of Formula I or any of Formula 1.1-1.16, wherein the compound is in substantially pure enantiomeric/diastereomeric form (i.e., substantially free from other enantiomers or diastereomers);
1.17. The compound of Formula I or any of 1.1-1.16, wherein the Compound has a enantiomeric or diastereomeric excess of greater than 70%, preferably greater than 80%, more preferably greater than 90% and most preferably greater than 95%; provided that when $R^2$ is H, $R^3$ is not H, and further provided that when $R^2$ is H, $R^3$ is not —C(O)—$R^4$ wherein $R^4$ is methyl.

In a further embodiment of the first aspect, the invention provides a compound of Formula I, in free or salt form as described in the following formulae:
2.1. The compound of Formula I or any of 1.1-1.17, wherein the salt is selected from a group consisting of hydrochloric, hydrobromic, sulfuric, phosphoric, nitric, acetic, propionic, succinic, glycolic, stearic, lactic, malic, tartaric, citric, ascorbic, palmitic, maleic, phenylacetic, glutamic, benzoic, salicylic, fumaric, toluenesulfonic, methanesulfonic, trifluoroacetic, sulfanilic, oxalic, and the like;
2.2. The compound of Formula I or Formula 2.1, wherein the salt is hydrochloric acid addition salt;

In the second aspect, the invention provides a pharmaceutical composition comprising the compound of Formula I, or any of 1.1-1.17 or 2.1-2.2 (the Compound of the Invention), in free or pharmaceutically acceptable salt form, in admixture with a pharmaceutically acceptable diluent or carrier.

In a further embodiment of the second aspect, the Pharmaceutical Composition of the Invention is for a sustained or delayed release, e.g., depot, formulation. In one embodiment, the depot formulation comprises the Compound of the Invention in a polymeric matrix. In another embodiment, the Compound of the Invention is dispersed or dissolved within the polymeric matrix. In a further embodiment, the polymeric matrix comprises standard polymers used in depot formulations such as polymers selected from a polyester of a hydroxyfatty acid and derivatives thereof, or a polymer of an alkyl alpha-cyanoacrylate, a polyalkylene oxalate, a poly(ortho ester), a polycarbonate, a poly(ortho carbonate), a poly(amino acid), a hyaluronic acid ester, and mixtures thereof. In a further embodiment, the polymer is selected from a group consisting of polylactide, poly d,l-lactide, polyglycolide, PLGA 50:50, PLGA 85:15 and PLGA 90:10 polymer. In another embodiment, the polymer is selected form poly(glycolic acid), poly-D,L-lactic acid, poly-L-lactic acid, copolymers of the foregoing, poly(aliphatic carboxylic acids), copolyoxalates, polycaprolactone, polydioxonone, poly(ortho carbonates), poly(acetals), poly(lactic acid-caprolactone), poly(ortho-esters), poly(glycolic acid-caprolactone), polyanhydrides, and natural polymers including albumin, casein, and waxes, such as, glycerol mono- and distearate, and the like. In a particular embodiment, the polymeric matrix comprises poly(d,l-lactide-co-glycolide). Any of the compositions hereinbefore described may be a pharmaceutical composition wherein said composition is in admixture with a pharmaceutically acceptable diluent or carrier.

The (Pharmaceutical) depot formulation as hereinbefore described are particularly useful for sustained or delayed release, wherein the Compound of the Invention is released upon degradation of the polymeric matrix. These Compositions may be formulated for controlled- and/or sustained-release of the Compounds of the Invention (e.g., as a depot composition) over a period of up to 180 days, e.g., from about 14 to about 30 to about 180 days. For example, the polymeric matrix may degrade and release the Compound of the Invention over a period of about 30, about 60 or about 90 days. In another example, the polymeric matrix may degrade and release the Compound of the Invention over a period of about 120, or about 180 days.

In still another further embodiment, the Pharmaceutical Compositions of the Invention, particularly the depot composition of the Invention is formulated for administration by injection. Long acting injectable formulations can also be achieved through milling of solid drug to the appropriate size particles.

In the third aspect, the invention provides the Compound of the Invention as hereinbefore described in an osmotic controlled release oral delivery system (OROS), which is described in WO 2000/35419 and EP 1 539 115 (U.S. Pub. No. 2009/0202631), the contents of each of which applications are incorporated by reference in their entirety. Therefore in one embodiment of the third aspect, the invention provides a pharmaceutical composition or device comprising (a) a gelatin capsule containing a Compound of the Invention in free or pharmaceutically acceptable salt form or a Pharmaceutical Composition of the Invention, as hereinbefore described; (b) a multilayer wall superposed on the gelatin capsule comprising, in outward order from the capsule: (i) a barrier layer, (ii) an expandable layer, and (iii) a semipermeable layer; and (c) and orifice formed or formable through the wall. (Composition P.1)

In another embodiment of the third aspect, the invention provides a composition comprising a gelatin capsule containing a liquid, the Compound of the Invention in free or pharmaceutically acceptable salt form or a Pharmaceutical Composition of the Invention as hereinbefore described, the gelatin capsule being surrounded by a composite wall comprising a barrier layer contacting the external surface of the gelatin capsule, an expandable layer contacting the barrier layer, a semi-permeable layer encompassing the expandable layer, and an exit orifice formed or formable in the wall. (Composition P.2)

In still another embodiment of the third aspect, the invention provides a composition comprising a gelatin capsule containing a liquid, the Compound of the Invention in free or pharmaceutically acceptable salt form or a Pharmaceutical Composition of the Invention as hereinbefore described, the gelatin capsule being surrounded by a composite wall comprising a barrier layer contacting the external surface of the gelatin capsule, an expandable layer contacting the barrier layer, a semipermeable layer encompassing the expandable layer, and an exit orifice formed or formable in the wall, wherein the barrier layer forms a seal between the expandable layer and the environment at the exit orifice. (Composition P.3)

In still another embodiment of the third aspect, the invention provides a composition comprising a gelatin capsule containing a liquid, the Compound of the Invention in free or pharmaceutically acceptable salt form or a Pharmaceutical Composition of the Invention as hereinbefore described, the gelatin capsule being surrounded by a barrier layer contacting the external surface of the gelatin capsule, an expandable layer contacting a portion of the barrier layer, a semi-permeable layer encompassing at least the expandable layer, and an exit orifice formed or formable in the dosage form extending from the external surface of the gelatin capsule to the environment of use. (Composition P.4). The expandable layer may be formed in one or more discrete sections, such as for example, two sections located on opposing sides or ends of the gelatin capsule.

In a particular embodiment of the third aspect, the Compound of the Invention in the Osmotic-controlled Release Oral delivery System (i.e., in Composition P.1-P.4) is in a liquid formulation, which formulation may be neat, liquid active agent, liquid active agent in a solution, suspension, emulsion or self-emulsifying composition or the like.

Further information on Osmotic-controlled Release Oral delivery System composition including characteristics of the gelatin capsule, barrier layer, an expandable layer, a semi-permeable layer; and orifice may be found in WO 2000/35419, the contents of which are incorporated by reference in their entirety. Other Osmotic-controlled Release Oral delivery Systems may be found in EP 1 539 115 (U.S. Pub. No. 2009/0202631), the contents of which are incorporated by reference in their entirety.

Therefore, in another embodiment of the third aspect, the invention provides a composition or device comprising (a) two or more layers, said two or more layers comprising a first layer and a second layer, said first layer comprises the Compound of the Invention, in free or pharmaceutically acceptable salt form, or a Pharmaceutical Composition as herein before described said second layer comprises a polymer; (b) an outer wall surrounding said two or more layers; and (c) an orifice in said outer wall. (Composition P.5)

Composition P.5 preferably utilizes a semi-permeable membrane surrounding a three-layer-core: in these embodiments the first layer is referred to as a first drug layer and contains low amounts of drug (e.g., the Compound of the Invention) and an osmotic agent such as salt, the middle layer referred to as the second drug layer contains higher amounts of drug, excipients and no salt; and the third layer referred to as the push layer contains osmotic agents and no drug. At least one orifice is drilled through the membrane on the first drug layer end of the capsule-shaped tablet. (Composition P.6)

Composition P.5 or P.6 may comprise a membrane defining a compartment, the membrane surrounding an inner protective subcoat, at least one exit orifice formed or formable therein and at least a portion of the membrane being semi-permeable; an expandable layer located within the compartment remote from the exit orifice and in fluid communication with the semi-permeable portion of the membrane; a first drug layer located adjacent the exit orifice; and a second drug layer located within the compartment between the first drug layer and the expandable layer, the drug layers comprising the Compound of the Invention in free or pharmaceutically acceptable salt thereof. Depending upon the relative viscosity of the first drug layer and second drug layer, different release profiles are obtained. It is imperative to identify the optimum viscosity for each layer. In the present invention, viscosity is modulated by addition of salt, sodium chloride. The delivery profile from the core is dependent on the weight, formulation and thickness of each of the drug layers. (Composition P.7)

In a particular embodiment, the invention provides Composition P.7 wherein the first drug layer comprising salt and the second drug layer containing no salt. Composition P.5-P.7 may optionally comprise a flow-promoting layer between the membrane and the drug layers. Compositions P.1-P.7 will generally be referred to as Osmotic-controlled Release Oral Delivery System Composition.

In a fourth aspect, the invention provides a method for the treatment or improvement of schizophrenia (Method I), including any of the negative, positive or general symptoms of schizophrenia, comprising administering to a patient in need thereof a compound of Formula I or 1.1-1.17, in free or pharmaceutically acceptable salt form as described in any of 2.1-2.2, or a hydrate or solvate thereof, or a pharmaceutical composition as described herein.

In a fifth aspect, the invention provides a method for the treatment or improvement of a psychiatric disorder (Method II), comprising administering to a patient in need thereof a compound of Formula I or 1.1-1.17, in free or pharmaceutically acceptable salt form as described in any of 2.1-2.2, or a hydrate or solvate thereof, or a pharmaceutical composition as described herein.

In a sixth aspect, the invention provides a method for the treatment or improvement of one or more central nervous system, gastrointestinal or cardiovascular diseases or disorders, including, for example, anxiety, depression or emotional abnormality, narcotic intoxication, narcotic addiction, sharp pain, dyskinesia, cerebrovascular disease, epilepsy, sleep disorders (including disorders of sleep duration, sleep onset latency, latency to persistent sleep, and distribution of slow wave sleep during sleep period), dementia including Alzheimer's disease, Parkinson's syndrome, brain tumor, attention deficit disorder, irritable bowel syndrome, irritable colon, spastic colon, colitis mucosus, enterocolitis, diverticulitis, dysentery, hypertension, arrhythmia, angina pectoris (Method III), comprising administering to a patient in need thereof a compound of Formula I or 1.1-1.17, in free or pharmaceutically acceptable salt form as described in any of 2.1-2.2, or a hydrate or solvate thereof, or a pharmaceutical composition as described herein.

DETAILED DESCRIPTION OF THE INVENTION

The present invention discloses compounds of Formula I.

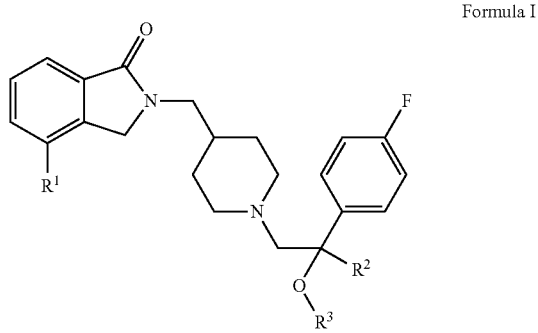

Formula I

In some embodiments of the invention, Compounds of the Invention are not themselves active moieties, but are rather pro-drugs of active moieties. The term "pro-drug" is a term recognized in the art, and it refers to a drug precursor prior to administration that generates or releases the active metabolite in vivo following administration, via some chemical or physiological process. In particular, Compounds of Formula I, wherein $R^3$ is H or $C_{1-6}$ alkyl (e.g., methyl), are active moieties, not pro-drugs. In contrast, Compounds of Formula I, wherein $R^3$ is a pharmaceutically acceptable and physiologically labile moiety, for example, wherein $R^3$ is —C(O)—$R^4$ and wherein such group —C(O)—$R^4$ is a physiologically labile moiety (e.g., $R^4$ is methyl or ethyl), will have weak activity or no activity. However, under physiological conditions these compounds will undergo hydrolysis to produce the active moiety Compounds of Formula I wherein $R^3$ is H, as well as a hydrolysis by-product, which is preferably not toxic at relevant concentrations (concentrations which would be provided by in vivo hydrolysis of a dosage of the pro-drug compound). For example, for a Compound of Formula I wherein $R^3$ is —C(O)—$R^4$, the hydrolysis products would be a Compound of Formula I wherein $R^3$ is H, and the other hydrolysis product would be a carboxylic acid of Formula $R^4$—C(O)—OH. Such physiologically labile moieties include, but are not limited to, carboxylic esters, for example wherein $R^4$ is a $C_{1-21}$ alkyl group. Under some physiological conditions, Compounds of Formula I, wherein $R^3$ is $C_{1-6}$ alkyl (e.g., methyl), may also under go in vivo conversion to the more active compound wherein $R^3$ is H, and therefore these compounds may be considered to be both active moieties and pro-drugs.

In a preferred embodiment of the invention, such pro-drug embodiments are selected from the group in which $R^4$ is chosen to result in a compound that undergoes physiologic hydrolysis at a therapeutically effective rate. One skilled in the art, will be able to select these groups to give Compounds of the Invention with a variety of physiologic rates of hydrolysis, solubility and membrane permeability characteristics, in order to achieve particular desired pharmacokinetic or pharmacodynamics properties.

In another preferred embodiment, the groups from which $R^4$ may be chosen based on the chemical, physical or toxicological properties of the by-product acids, of the formula $R^4$—C(O)—OH, which results from hydrolysis of the pro-drug compounds. In some embodiments, the groups may be chosen so that hydrolysis of the pro-drug produces a pharmacologically acceptable pro-moiety, e.g. one that is non-toxic and rapidly excreted and for the quantities generated in the course of therapeutic treatment. Such commonly used pro-moieties include acetic acid, butyric acid, isobutyric acid, pivalic acid, and such naturally occurring fatty acids as stearic acid, lauric acid, palmitic acid, arachidonic acid, linoleic acid, linolenic acid and oleic acid.

The compounds of Formula I may comprise one or more chiral carbon atoms. The compounds may thus exist in individual isomeric, e.g., enantiomeric or diastereomeric forms or as mixtures of individual forms, e.g., racemic/enantiomeric/diastereomeric mixtures. Any isomer may be present in which the asymmetric center is in the (R)-, (S)-, or (R,S)-configuration. The invention is to be understood as embracing both individual optically active isomers as well as mixtures (e.g., racemic/enantiomeric/diastereomeric mixtures) thereof. Accordingly, the Compounds of the Invention may be a racemic mixture or it may be predominantly, e.g., in pure, or substantially pure, isomeric form, e.g., greater than 70% enantiomeric/diastereomeric excess ("ee"), preferably greater than 80% ee, more preferably greater than 90% ee, most preferably greater than 95% ee. The purification of said isomers and the separation of said isomeric mixtures may be accomplished by standard techniques known in the art (e.g., column chromatography, preparative TLC, preparative HPLC, simulated moving bed and the like).

As used herein, the term "schizophrenia" covers the full spectrum of schizophrenic disorders known to those skilled in the art. These include, but are not limited to, the following disorders: catatonic, disorganized, paranoid, residual and undifferentiated schizophrenia; schizophreniform disorder and schizoaffective disorder.

The term "receptor", as used herein, means a membrane-binding type receptor, as well as other binding sites. For example, the existence of at least two sigma receptor subtypes has been proposed, i.e., sigma 1 and sigma 2, and classification of sigma binding sites has been proposed.

The term "subject" refers to any animal, including mammals, such as, but not limited to, humans, mice, rats, other rodents, rabbits, dogs, cats, pigs, cattle, sheep, horses, or primates.

The term "treating" (and corresponding terms "treat" and "treatment") includes palliative, restorative, and/or preventative ("prophylactic") treating of a subject. The term "palliative treating" refers to treatment that eases or reduces the effect or intensity of a condition in a subject without curing the condition. The term "preventative treating" (and the corresponding term "prophylactic treating") refers to treatment that prevents the occurrence of a condition in a subject. The term "restorative treating" ("curative") refers to treatment that halts the progression of, reduces the pathologic manifestations of or entirely eliminates a condition in a subject. Treating can be done with a therapeutically effective amount of compound, salt or composition that elicits the biological or medicinal response of a tissue, system or subject that is being sought by an individual such as a researcher, doctor, veterinarian, or clinician. In one embodiment of the invention, treatment refers to the amelioration of symptoms associated with a disease or disorder with or without treatment of the cause of the disease or disorder.

In one aspect of the present invention, compounds of Formula I have properties useful to treat schizophrenia and/or one or more symptoms of schizophrenia. In an aspect, compounds of Formula I are useful to treat one or more negative symptoms of schizophrenia. In another aspect, compounds of Formula I are useful to treat one or more negative symptoms of schizophrenia while not affecting one or more positive symptoms of schizophrenia. In another aspect, compounds of Formula I are useful to treat one or more negative symptoms of schizophrenia while also treating one or more positive symptoms of schizophrenia. In another aspect, compounds of Formula I are useful to treat one or more negative symptoms of schizophrenia while also treating one or more general symptoms of schizophrenia. In yet another aspect, compounds of Formula I are useful to treat one or more positive symptoms of schizophrenia.

In another aspect, compounds of Formula I are useful for augmenting treatment of schizophrenia in a subject presently receiving one or more compounds for the treatment of schizophrenia. In yet another aspect, compounds of Formula I are useful for treating schizophrenia in combination with one or more additional antipsychotic compounds. In still another aspect, compounds of Formula I are useful for treating schizophrenia in combination with one or more additional antipsychotic compounds, by decreasing the therapeutically effective dosage of the one or more antipsychotic compounds. In one aspect, compounds of Formula I are useful for treating schizophrenia in combination with one or more additional antipsychotic compounds by decreasing the therapeutically effective dosage of the one or more antipsychotic compounds, wherein the dosage of the compound of Formula I is also decreased.

In an another aspect, compounds of Formula I are useful for augmenting treatment of schizophrenia in a subject presently receiving one or more compounds for the treatment of schizophrenia by treating one or more negative symptoms of schizophrenia. In an embodiment, compounds of Formula I are useful for treating schizophrenia in combination with one or more additional antipsychotic compounds, by improving at least one aspect and/or parameter of sleep in the subject.

In another aspect, compounds of Formula I may be useful for treating or improving the symptoms of other psychiatric disorders that are normally related dysregulation of 5-HT$_{2A}$ and sigma receptor binding, such as but not limited to, obesity, anxiety, depression, psychosis, sleep disorders, sexual disorders, migraine, conditions associated with cephalic pain, social phobias and some gastrointestinal disorders, such as GI motility disorders.

In an aspect, compounds of Formula I disclosed herein have a receptor binding profile demonstrating preferential binding for sigma 1 receptors or sigma 2 receptors, 5-HT$_{2A}$ receptors, and $\alpha_1$ adrenergic receptors. In another aspect, compounds of Formula I have a receptor binding profile comprising preferential affinity for sigma 2 receptors, while demonstrating little or no affinity for sigma 1 receptors. In yet another aspect, compounds of Formula I have a receptor binding profile comprising preferential affinity for sigma 2 receptors over sigma 1 receptors. In yet another aspect, compounds of Formula I have a receptor binding profile comprising preferential affinity for sigma 1 receptors over sigma 2 receptors. In yet another aspect, compounds of Formula I have a receptor binding profile showing comparable affinity for sigma 2 receptors and sigma 1 receptors. However, it will be understood that certain compounds of Formula I may not have a preferential binding for the same panel of receptors, and in some instances, may demonstrate preferential binding for one or more different receptors, including fewer than all of the sigma 1, sigma 2, 5-HT$_{2A}$, and $\alpha_1$ adrenergic receptors. In another aspect, compounds of Formula I disclosed herein may have little or no affinity for dopaminergic, muscarinic, cholinergic or histaminergic receptors, and may have varying affinities for any combinations of those receptors.

In an embodiment, a method is provided for treating schizophrenia in a subject comprising administering to a subject in need thereof a therapeutically effective amount of a compound of the Formula I or a pharmaceutically acceptable salt, hydrate, or solvate thereof, or a pharmaceutical composition, as described herein.

In one embodiment, a method is provided for treating at least one negative symptom of schizophrenia in a subject comprising administering to a subject in need thereof a therapeutically effective amount of a compound of the Formula I or a pharmaceutically acceptable salt, or a pharmaceutical composition, as described herein.

In an embodiment, a method is provided for treating at least one negative symptom of schizophrenia in a subject comprising administering to a subject in need thereof a therapeutically effective amount of a compound of the Formula I or a pharmaceutically acceptable salt, or a pharmaceutical composition, as described herein, wherein the at least one negative symptom is treated. In an embodiment, at least one primary negative symptom is treated. In another embodiment, at least one secondary negative symptom is treated. In an embodiment, at least one disorder of sleep is treated. In another embodiment, at least one aspect or parameter of sleep is improved in a patient. In an embodiment, sleep is improved in a schizophrenic patient.

In an aspect, the disruption of at least one disorder or parameter of sleep is associated with schizophrenia. In an embodiment, the disruption of the at least one disorder or parameter of sleep is a negative symptom of schizophrenia. In another embodiment, the disruption of the at least one disorder or parameter of sleep is neither a positive nor a negative symptom of schizophrenia, but rather, is merely associated with the schizophrenia. The present disclosure provides for treatment of at least one disorder or parameter of sleep regardless of how the disorder or affected parameter of sleep arises.

In an embodiment, sleep is improved in a patient who does not have schizophrenia, In an aspect, at least one disorder or parameter of sleep is treated and/or improved. In an aspect, a method is provided for improving at least one aspect of sleep, comprising administering to a subject in need thereof a therapeutically effective amount of a compound of Formula I or a pharmaceutically acceptable salt thereof, as set forth above. Various aspects of sleep may be treated, including, but not limited to, sleep onset latency, latency to persistent sleep, and the distribution of slow wave sleep across the sleep period time, or one or more segments of sleep period time. In an aspect, total sleep time is decreased. In an aspect, sleep efficiency index is decreased, duration of wake after sleep onset is increased, or slow wave sleep in increased or decreased.

In an embodiment, a method is provided for treating at least one negative symptom of schizophrenia in a subject comprising administering to a subject in need thereof a therapeutically effective amount of a compound of the Formula I or a pharmaceutically acceptable salt, or a pharmaceutical composition, as described herein, wherein the at least one negative symptom is treated, further wherein at least one positive symptom of schizophrenia is not treated. In another embodiment, a method is provided for treating at least one negative symptom of schizophrenia in a subject comprising administering to a subject in need thereof a therapeutically effective amount of a compound of the Formula I or a pharmaceutically acceptable salt, or a pharmaceutical composition, as described herein, wherein the at least one negative symptom is treated, further wherein at least one positive symptom of schizophrenia is also treated.

In another embodiment, a method is provided for treating at least one negative symptom of schizophrenia in a subject comprising administering to a subject in need thereof a therapeutically effective amount of a compound of the Formula I or a pharmaceutically acceptable salt, or a pharmaceutical composition, as described herein, wherein the at least one negative symptom is treated, further wherein a general symptom of schizophrenia is not treated. In an embodiment, a method is provided for treating at least one negative symptom of schizophrenia in a subject comprising administering to a subject in need thereof a therapeutically effective amount of a compound of the Formula I or a pharmaceutically acceptable salt, or a pharmaceutical composition, as described herein, wherein the at least one negative symptom is treated, further wherein at least one general symptom of schizophrenia is treated.

In an embodiment, a method is provided for treating or improving cognition, comprising administering to a subject in need thereof a therapeutically effective amount of a compound of Formula I or a pharmaceutically acceptable salt thereof, as set forth herein. As will be understood based on the disclosure herein, modification of sleep parameters can improve cognition. In an aspect, cognition in general is improved. In another aspect, one or more aspects of cognition are improved, including, among others, memory consolidation, executive functions, verbal memory and verbal fluency.

In an embodiment, a method is provided for treating or improving at least one aspect or parameter of sleep, comprising administering to a subject in need thereof a therapeutically effective amount of a compound of the Formula I or a pharmaceutically acceptable salt, as set forth above, wherein the subject is affected with schizophrenia. In an aspect, a disorder of sleep is treated.

Negative symptoms of schizophrenia include, but are not limited to, blunted affect, emotional withdrawal, poor rapport, passive/apathetic social withdrawal, difficulty in abstract thinking, lack of spontaneity and flow of conversation, and stereotyped thinking. Positive symptoms of schizophrenia include, but are not limited to, delusions, conceptual disorganization, hallucinations, hyperactivity and excitement, grandiosity, suspiciousness and feelings of persecution, hostility, and nonverbal expression of anger and resentment, including sarcasm, passive aggressive behavior, verbal abuse and assaultiveness. General symptoms of schizophrenia include, but are not limited to, somatic concern, anxiety, guilt-feelings, tension, mannerisms and posturing, depression, motor retardation, uncooperativeness, unusual thought content, disorientation, poor attention, lack of judgment and insight, disturbance of volition, poor impulse control, preoccupation, and active social avoidance.

Dosage Forms and Amounts

For therapeutic administration according to the present invention, a compound of Formula I may be employed in the form of its free base, but is preferably used in the form of a pharmaceutically acceptable salt, typically the hydrochloride salt.

Alternative salts of a compound of Formula I with pharmaceutically acceptable acids may also be utilized in therapeutic administration, for example salts derived from the functional free base and an organic or inorganic acid, for example including, but not limited to, palmitic acid, hydrobromic acid, phosphoric acid, acetic acid, fumaric acid, maleic acid, salicylic acid, citric acid, oxalic acid, lactic acid, malic acid, methanesulfonic acid, p-toluenesulfonic acid, sulfuric acid, trifluoroacetic acid, tartaric acid, ascorbic acid, glutamic acid, benzoic acid, and sulfanilic acid.

All solvates and all alternative physical forms of a compound of Formula I or its pharmaceutically acceptable derivatives as described herein, including but not limited to alternative crystalline forms, amorphous forms and polymorphs, are also within the scope of this invention, and all references to a compound of Formula I herein include all pharmaceutically acceptable salts, and all solvates and alternative physical forms thereof.

For therapeutic administration, a compound of Formula I or a pharmaceutically acceptable salt thereof, may be administered in pure form, but will preferably be formulated into any suitable pharmaceutically acceptable and effective composition which provides effective levels of the active ingredient in the body.

Such pharmaceutically acceptable and effective compositions may be formulated for administration by any satisfactory route, including, including orally, parenterally (intravenous, intramuscular or subcutaneous) or transdermally, but are preferably administered orally. In certain embodiment, such as in depot formulations, the compound of the invention is preferably administered parenterally.

The compounds of Formula I may be administered as a depot formulation, e.g., by dispersing, dissolving or encapsulating the compounds in a polymeric matrix, such that the compound is continually released as the polymer degrades over time. The release of the compounds of Formula I from the polymeric matrix provides for the controlled- and/or delayed- and/or sustained-release of the compounds, e.g., from the pharmaceutical depot composition, into a subject, for example a warm-blooded animal such a human, to which the pharmaceutical depot is administered. Thus, the pharmaceutical depot delivers the compounds of the invention to the subject at concentrations effective for treatment of the particular disease or medical condition over a sustained period of time, e.g., 14-180 days, preferably about 30, about 60 or about 90 days.

Polymers useful for the polymeric matrix in the depot composition of the invention may include a polyester of a hydroxyfatty acid and derivatives thereof or other agents such as polylactic acid, polyglycolic acid, polycitric acid, polymalic acid, poly-beta.-hydroxybutyric acid, epsilon-caprolactone ring opening polymer, lactic acid-glycolic acid copolymer, 2-hydroxybutyric acid-glycolic acid copolymer, polylactic acid-polyethyleneglycol copolymer or polyglycolic acid-polyethyleneglycol copolymer), a polymer of an alkyl alpha-cyanoacrylate (for example poly(butyl 2-cyanoacrylate)), a polyalkylene oxalate (for example polytrimethylene oxalate or polytetramethylene oxalate), a poly(ortho ester), a polycarbonate (for example polyethylene carbonate or polyethylenepropylene carbonate), a poly(ortho carbonate), a poly(amino acid) (for example poly-gamma.-L-alanine, poly-.gamma.-benzyl-L-glutamic acid or poly-y-methyl-L-glutamic acid), a hyaluronic acid ester, and the like, and one or more of these polymers can be used.

If the polymers are copolymers, they may be any of random, block and/or graft copolymers. When the above alpha-hydroxycarboxylic acids, hydroxydicarboxylic acids and hydroxytricarboxylic acids have optical activity in their molecules, any one of D-isomers, L-isomers and/or DL-isomers may be used. Among others, alpha-hydroxycarboxylic acid polymer (preferably lactic acid-glycolic acid polymer), its ester, poly-alpha-cyanoacrylic acid esters, etc. may be used, and lactic acid-glycolic acid copolymer (also referred to as poly(lactide-alpha-glycolide) or poly(lacticco-glycolic acid), and hereinafter referred to as PLGA) are preferred. Thus, in one aspect the polymer useful for the polymeric matrix is PLGA. As used herein, the term PLGA includes polymers of lactic acid (also referred to as polylactide, poly(lactic acid), or PLA). Most preferably, the polymer is the biodegradable poly(d,l-lactide-co-glycolide) polymer.

In a preferred embodiment, the polymeric matrix of the invention is a biocompatible and biodegradable polymeric material. The term "biocompatible" is defined as a polymeric material that is not toxic, is not carcinogenic, and does not significantly induce inflammation in body tissues. The matrix material should be biodegradable wherein the polymeric material should degrade by bodily processes to products readily disposable by the body and should not accumulate in the body. The products of the biodegradation should also be biocompatible with the body in that the polymeric matrix is biocompatible with the body. Particular useful examples of polymeric matrix materials include poly (glycolic acid), poly-D,L-lactic acid, poly-L-lactic acid, copolymers of the foregoing, poly(aliphatic carboxylic acids), copolyoxalates, polycaprolactone, polydioxonone, poly(ortho carbonates), poly(acetals), poly(lactic acid-caprolactone), polyorthoesters, poly(glycolic acid-caprolactone), polyanhydrides, and natural polymers including albumin, casein, and waxes, such as, glycerol mono- and distearate, and the like. The preferred polymer for use in the practice of this invention is dl-(polylactide-co-glycolide), which is referred to as PLGA polymer. It is preferred that the molar ratio of lactide to glycolide in such a copolymer be in the range of from about 75:25 to 50:50.

Useful PLGA polymers may have a weight-average molecular weight of from about 5,000 to 500,000 daltons, preferably about 150,000 daltons. Dependent on the rate of degradation to be achieved, different molecular weight of polymers may be used. For a diffusional mechanism of drug release, the polymer should remain intact until all of the drug is released from the polymeric matrix and then degrade. The drug can also be released from the polymeric matrix as the polymeric excipient bioerodes.

The PLGA may be prepared by any conventional method, or may be commercially available. For example, PLGA can be produced by ring-opening polymerization with a suitable catalyst from cyclic lactide, glycolide, etc. (see EP-0058481B2; Effects of polymerization variables on PLGA properties: molecular weight, composition and chain structure).

It is believed that PLGA is biodegradable by means of the degradation of the entire solid polymer composition, due to the break-down of hydrolysable and enzymatically cleavable ester linkages under biological conditions (for example in the presence of water and biological enzymes found in tissues of warm-blooded animals such as humans) to form lactic acid and glycolic acid. Both lactic acid and glycolic acid are water-soluble, non-toxic products of normal metabolism, which may further biodegrade to form carbon dioxide and water. In other words, PLGA is believed to degrade by means of hydrolysis of its ester groups in the presence of water, for example in the body of a warm-blooded animal such as man, to produce lactic acid and glycolic acid and create the acidic microclimate. Lactic and glycolic acid are by-products of various metabolic pathways in the body of a warm-blooded animal such as man under normal physiological conditions and therefore are well tolerated and produce minimal systemic toxicity.

In another embodiment, the polymeric matrix useful for the invention may comprise a star polymer wherein the structure of the polyester is star-shaped. These polyesters have a single polyol residue as a central moiety surrounded by acid residue chains. The polyol moiety may be, e. g., glucose or, e. g., mannitol. These esters are known and described in GB 2,145,422 and in U.S. Pat. No. 5,538,739, the contents of which are incorporated by reference.

The star polymers may be prepared using polyhydroxy compounds, e. g., polyol, e. g., glucose or mannitol as the initiator. The polyol contains at least 3 hydroxy groups and has a molecular weight of up to about 20,000 daltons, with at least 1, preferably at least 2, e. g., as a mean 3 of the hydroxy groups of the polyol being in the form of ester groups, which contain polylactide or co-polylactide chains. The branched polyesters, e. g., poly (d, l-lactide-co-glycolide) have a central glucose moiety having rays of linear polylactide chains.

The depot composition of the invention as hereinbefore described may comprise the polymer in the form of microparticles or nanoparticles, or in a liquid form, with the Compounds of the Invention dispersed or encapsulated therein. "Microparticles" is meant to mean solid particles that contain the Compounds of the Invention either in solution or in solid form wherein such compound is dispersed or dissolved within the polymer that serves as the matrix of the particle. By an appropriate selection of polymeric materials, a microparticle formulation can be made in which the resulting microparticles exhibit both diffusional release and biodegradation release properties.

When the polymer is in the form of microparticles, the microparticles may be prepared using any appropriate method, such as by a solvent evaporation or solvent extraction method. For example, in the solvent evaporation method, the Compounds of the Invention and the polymer may be dissolved in a volatile organic solvent (for example a ketone such as acetone, a halogenated hydrocarbon such as chloroform or methylene chloride, a halogenated aromatic hydrocarbon, a cyclic ether such as dioxane, an ester such as ethyl acetate, a nitrile such as acetonitrile, or an alcohol such as ethanol) and dispersed in an aqueous phase containing a suitable emulsion stabilizer (for example polyvinyl alcohol, PVA). The organic solvent is then evaporated to provide microparticles with the Compounds of the Invention encapsulated therein. In the solvent extraction method, the Compounds of the Invention and polymer may be dissolved in a polar solvent (such as acetonitrile, dichloromethane, methanol, ethyl acetate or methyl formate) and then dispersed in an aqueous phase (such as a water/PVA solution). An emulsion is produced to provide microparticles with the Compounds of the Invention encapsulated therein. Spray drying is an alternative manufacturing technique for preparing the microparticles.

Another method for preparing the microparticles of the invention is also described in both U.S. Pat. No. 4,389,330 and U.S. Pat. No. 4,530,840.

The microparticle of the present invention can be prepared by any method capable of producing microparticles in a size range acceptable for use in an injectable composition. One preferred method of preparation is that described in U.S. Pat. No. 4,389,330. In this method the active agent is dissolved or dispersed in an appropriate solvent. To the agent-containing medium is added the polymeric matrix material in an amount relative to the active ingredient that provides a product having the desired loading of active agent. Optionally, all of the ingredients of the microparticle product can be blended in the solvent medium together.

Solvents for the compounds of the invention and the polymeric matrix material that can be employed in the practice of the present invention include organic solvents, such as acetone; halogenated hydrocarbons, such as chloroform, methylene chloride, and the like; aromatic hydrocarbon compounds; halogenated aromatic hydrocarbon compounds; cyclic ethers; alcohols, such as, benzyl alcohol; ethyl acetate; and the like. In one embodiment, the solvent for use in the practice of the present invention may be a mixture of benzyl alcohol and ethyl acetate. Further information for the preparation of microparticles useful for the invention can be found in U.S. Patent Publication Number 2008/0069885, the contents of which are incorporated herein by reference in their entirety.

The amount of the compounds of formula I incorporated in the microparticles usually ranges from about 1 wt. % to about 90 wt. %, preferably 30 to 50 wt. %, more preferably 35 to 40 wt. %. By weight % is meant parts of the Compounds of the Invention per total weight of microparticle.

The pharmaceutical depot may comprise a pharmaceutically-acceptable diluent or carrier, such as a water miscible diluent or carrier.

Details of general Osmotic-controlled Release Oral delivery System composition may be found in EP 1 539 115 (U.S. Pub. No. 2009/0202631) and WO 2000/35419, the contents of each of which are incorporated by reference in their entirety.

A "therapeutically effective amount" is any amount of the compounds of the invention (for example as contained in the pharmaceutical depot) which, when administered to a subject suffering from a disease or disorder, is effective to cause a reduction, remission, or regression of the disease or disorder over the period of time as intended for the treatment.

Dosages employed in practicing the present invention will of course vary depending, for example, on the particular disease or condition to be treated, the particular compound of the invention used, the mode of administration, and the therapy desired. Unless otherwise indicated, an amount of the compound of the invention for administration (whether administered as a free base or as a salt form) refers to or is based on the amount of the compound of the invention in free base form (i.e., the calculation of the amount is based on the free base amount). However, if the compound of the invention contains a physiologically labile moiety for $R^3$, then the amount of the compound of the invention for administration is based on the equivalent amount of the fully hydrolyzed product of cleavage of the labile moiety as its free base.

Pharmaceutical compositions comprising compounds of the invention may be prepared using conventional diluents or excipients (an example include, but is not limited to, sesame oil) and techniques known in the galenic art. Thus oral dosage forms may include tablets, capsules, solutions, suspensions and the like.

In an aspect, a method of administering a compound of formula I may include titration of the compound up to a predetermined level. In one embodiment, a compound is used at a specified level (e.g., 2 mg bid., 4 mg bid., 8 mg bid., 16 mg bid.). In one embodiment, the compound is titrated up to a predetermined dosage (e.g., titration up to 16 mg bid., 32 mg bid., 64 mg bid., etc. . . . ).

Administration of a compound for any purpose as described herein, in any form or combination described herein, may include administering the compound of Formula I or a pharmaceutically acceptable salt thereof, at a dose of between 10 ng-1 g, 100 ng-750 mg, 500 ng-500 mg, 10 µg-200 mg, 15 µg-190 mg, 25 µg-180 mg, 50 µg-170 mg, 75 µg-160 mg, 100 µg-150 mg, 250 µg-140 mg, 400 µg-130 mg, between 500 µg-128 mg, 600 µg-100 mg, 750 µg-75 mg, 900 µg-50 mg, or at a dose between 1 mg-64 mg. The treatment of schizophrenia may include administering the compound of Formula I or a pharmaceutically acceptable salt thereof at a dose of <1 g, <500 mg, <200 mg, <150 mg, <100 mg, <50 mg, <40 mg, <30 mg, <20 mg, <10 mg, <9 mg, <8 mg, <7 mg, <6 mg, <5 mg, <4 mg, <3 mg, <2 mg, <1 mg, <0.5 mg, <0.25 mg, <0.1 mg, <0.05 mg, or <0.01 mg, <0.005 mg, or <0.001 mg. The dose may be administered as a weekly dose, a dose every other day, a single daily dose, twice daily, three times daily, four times daily, five times daily, or more frequently. In an embodiment, the compound of Formula I or a pharmaceutically acceptable salt thereof is administered at a dose of between 8 mg 32 mg twice daily.

In an embodiment, a compound of Formula I or a pharmaceutically acceptable salt thereof, or a pharmaceutical composition as described herein, is administered independently of any other medication.

Co-Administration of Compounds

In another embodiment, a compound of Formula I or a pharmaceutically acceptable salt thereof is administered in conjunction with one or more other medications. Such other medications may be administered or co-administered in forms and dosages as known in the art, or in the alternative, as has been described above for administration of compounds of Formula I.

A compound of Formula I, for example, or a pharmaceutically acceptable salt of either, may advantageously be administered in combination with at least one neuroleptic agent (e.g., a typical or an atypical anti-psychotic agent) to provide improved treatment of any combination of negative symptoms of schizophrenia, positive symptoms of schizophrenia, general symptoms of schizophrenia, or the treatment of schizophrenia itself. The combinations, uses and methods of treatment of the invention may also provide advantages in treatment of patients who fail to respond adequately or who are resistant to other known treatments.

In an embodiment, a compound of Formula I may be administered to a patient already undergoing treatment with at least one neuroleptic agent (e.g., a typical or an atypical antipsychotic agent), to provide improved treatment of any combination of negative symptoms of schizophrenia, positive symptoms of schizophrenia, general symptoms of schizophrenia, or the treatment of schizophrenia itself.

Atypical anti-psychotics include, but are not limited to, olanzapine, clozapine, risperidone, paliperidone, aripiprazole, quetiapine, iloperidone, ziprasidone, asenapine, lurasidone, sertindole, amisulpride, clotiapine, mosapramine, perospirone, sulpiride, and zotepine. Typical antipsychotics include, but are not limited to, haloperidol, benperidol, loxapine, molindone, pimozide, thioridazine, mesoridazine, thiothixene, chlorprothixene, fluphenazine, trifluoperazine, chlorpromazine, perphenazine, prochlorperazine, droperidol, and zuclopenthixol. Other neuroleptic agents include 1-(4-fluorophenyl)-4-((6bR,10aS)-3-methyl-2,3,6b,7,10, 10a-hexahydro-1H-pyrido[3',4':4,5]pyrrolo[1,2,3-de]quinoxalin-8(9H)-yl)butan-1-one, 1-(4-fluorophenyl)-4((6bR, 10aS)-3-methyl-2,3,6b,7,10,10a-hexahydro-1H-pyrido[3', 4':4,5]pyrrolo[1,2,3-de]quinoxalin-8(9H)-yl)butan-1-ol, as well as any one of the compounds disclosed in WO 2011/133224 and WO 2013/155505, the contents of each of which are incorporated by reference.

In another aspect, the Invention includes administration to a patient of a compound of Formula I, wherein $R^2$ and $R^3$ are both H, or wherein $R^2$ is H and $R^3$ is —OC(O)—$R^4$ and $R^4$ is methyl, in combination with 1-(4-fluorophenyl)-4-46bR, 10aS)-3-methyl-2,3,6b,7,10,10a-hexahydro-1H-pyrido[3', 4':4,5]pyrrolo[1,2,3-de]quinoxalin-8(9H)-yl)butan-1-one, 1-(4-fluorophenyl)-44(6bR,10aS)-3-methyl-2,3,6b,7,10, 10a-hexahydro-1H-pyrido[3',4':4,5]pyrrolo[1,2,3-de]quinoxalin-8(9H)-yl)butan-1-ol and/or any one of the compounds disclosed in WO 2011/133224 and WO 2013/155505, in free or pharmaceutically acceptable salt form.

Augmentation of Treatment of Symptoms and Schizophrenia

In an embodiment, a compound of Formula I may be administered to a patient in conjunction with at least one neuroleptic agent, or to a patient already undergoing treatment with at least one neuroleptic agent, to provide improved treatment of any combination of negative symptoms of schizophrenia, positive symptoms of schizophrenia, general symptoms of schizophrenia, or the treatment of schizophrenia itself. In an embodiment, the administration of a compound of Formula I lowers the concentration of the neuroleptic agent required to achieve a therapeutically effective amount of the neuroleptic agent. In an aspect, the compound of Formula I provides a synergistic effect to the neuroleptic agent.

In an embodiment, a compound of Formula I may be administered to a patient in conjunction with at least one neuroleptic agent, or to a patient already undergoing treatment with at least one neuroleptic agent, wherein the neuroleptic agent does not prolong the QT interval. Such neuroleptic agents include, but are not limited to, risperidone, quetiapine, aripiprazole, and olanzapine, and pharmaceutically acceptable salts thereof, including, but not limited to, palmitate salts. In an aspect, a compound of Formula I, will be paired with one or more antipsychotic compounds having a low QT prolongation liability. It will be clear to the skilled artisan how to select, identify and/or characterize the QT prolongation liability of an antipsychotic, particularly in view of the guidance set forth herein.

In an embodiment, a compound of Formula I may be administered to a patient in conjunction with at least one neuroleptic agent, or to a patient already undergoing treatment with at least one neuroleptic agent, wherein the administration of the compound of Formula I further augments the treatment of at least one negative symptom of schizophrenia. In another embodiment, a compound of Formula I may be administered to a patient in conjunction with at least one neuroleptic agent, or to a patient already undergoing treatment with at least one neuroleptic agent, wherein the administration of the compound of Formula I further augments the treatment of any combination of at least one negative symptom of schizophrenia, at least one positive symptom of schizophrenia, at least one general symptom of schizophrenia, or the schizophrenia itself.

In an embodiment, a method is provided for treating at least one negative symptom of schizophrenia in a subject comprising administering to a subject in need thereof a therapeutically effective amount of a compound of the Formula I or a pharmaceutically acceptable salt, or a pharmaceutical composition as described herein, wherein the at least one negative symptom is treated, further wherein schizophrenia-related cognition is improved. Cognitive skills include, but are not limited to, motor speed, verbal memory, and verbal fluency. Improvement of cognition is described in greater detail elsewhere herein.

In an embodiment, sleep is improved in a patient who does not have schizophrenia. In an aspect, at least one disorder or parameter of sleep is treated and/or improved. In another aspect, a method is provided for improving at least one aspect of sleep, comprising administering to a subject in need thereof a therapeutically effective amount of a compound of the Formula I or a pharmaceutically acceptable salt, or a pharmaceutical composition, as described herein. Various aspects of sleep may be treated, including, but not limited to, sleep onset latency, latency to persistent sleep, and the distribution of slow wave sleep across the sleep period time, or one or more segments of sleep period time. In another aspect, total sleep time is decreased. In an aspect, sleep efficiency index (SEI) is decreased. In another aspect, the duration of wake after sleep onset (WASO) is increased. In another aspect, slow wave sleep (SWS) is increased in the first third of sleep period time (SPT 1). In another aspect, SWS is decreased in the last third of SPT (SPT3).

In an embodiment, a method is provided for treating or improving cognition, comprising administering to a subject in need thereof a therapeutically effective amount of a compound of the Formula I or a pharmaceutically acceptable salt, or a pharmaceutical composition, as described herein. As will be understood based on the disclosure herein, modification of sleep parameters can improve cognition. By way of a non-limiting example, improvement and/or an increase in SWS improves cognition. In an aspect, cognition in general is improved. In another aspect, one or more aspects of cognition are improved, including, among others, memory consolidation, executive functions, verbal memory, and verbal fluency.

In an embodiment, a method is provided for treating or improving at least one aspect or parameter of sleep, comprising administering to a subject in need thereof a therapeutically effective amount of a compound of the Formula I or a pharmaceutically acceptable salt, or a pharmaceutical composition, as described herein, wherein the subject is affected with schizophrenia. In another aspect, a disorder of sleep is treated.

In an embodiment, a method is provided for treating or improving psychiatric disorders related to $5HT_{2A}$ and sigma receptor binding dysregulation, such as but not limited to, obesity, anxiety, depression, psychosis, sleep disorders, sexual disorders, migraine, conditions associated with cephalic pain, social phobias and some gastrointestinal disorders, such as GI motility disorders, comprising administering to a subject in need thereof a therapeutically effective amount of a compound of the Formula I or a pharmaceutically acceptable salt, or a pharmaceutical composition, as described herein.

As used herein, the term "Alkyl" is a saturated or unsaturated hydrocarbon moiety, e.g., 1 to 21 carbon atoms in length, which may be linear or branched (e.g., n-butyl or tert-butyl), preferably linear, unless otherwise specified. In another embodiment, any one or more of the methylene units of the alkyl chain may be optionally replaced by an —O—, —NH— or —S—.

It is also intended that the Compounds of the Invention encompass their stable and unstable isotopes. Stable isotopes are nonradioactive isotopes which contain one additional neutron compared to the abundant nuclides of the same species (i.e., element). It is expected that the activity of compounds comprising such isotopes would be retained, and such compound would also have utility for measuring pharmacokinetics of the non-isotopic analogs. For example, the hydrogen atom at a certain position on the Compounds of the Invention may be replaced with deuterium (a stable isotope which is non-radioactive). Examples of known stable isotopes include, but not limited to, deuterium, $^{13}C$, $^{15}N$, $^{18}O$. Alternatively, unstable isotopes, which are radioactive isotopes which contain additional neutrons compared to the abundant nuclides of the same species (i.e., element), e.g., $^{123}$I $^{131}$I, $^{125}$I, $^{11}$C, $^{18}$F, may replace the corresponding abundant species of I, C and F. Another example of useful isotope of the compound of the invention is the $^{11}$C isotope. These radio isotopes are useful for radio-imaging and/or pharmacokinetic studies of the compounds of the invention.

The pharmaceutically acceptable salts of the Compounds of the Invention can be synthesized from the parent compound which contains a basic or acidic moiety by conventional chemical methods. Generally, such salts can be prepared by reacting the free base forms of these compounds with a stoichiometric amount of the appropriate acid in water or in an organic solvent, or in a mixture of the two; generally, non-aqueous media such as ether, ethyl acetate, ethanol, isopropanol, or acetonitrile is preferred. Further details for the preparation of these salts, e.g., toluenesulfonic salt in amorphous or crystal form, may be found in PCT/US08/03340 and/or U.S. Provisional Appl. No. 61/036,069.

Methods of Making the Compounds of the Invention:

The compounds of Formula I may be prepared from the compounds of Formula II, wherein R$^1$ is H or F. The compounds of Formula II, wherein R$^1$ is H or F, may be prepared as described in U.S. Pat. No. 7,166,617, Examples 1 and 6, respectively.

Formula II

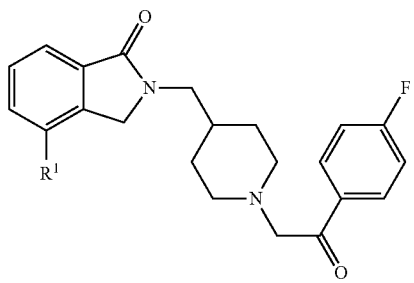

Specifically, the compounds of the present invention can be prepared from either the compound of Formula III or the compound of Formula IV, disclosed in the above patent as compounds number 1 and 10, respectively, the synthetic procedures for which can be found in Example 1 and 6, respectively, of the '617 patent.

Formula III

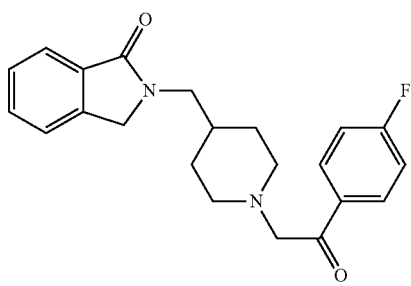

Formula IV

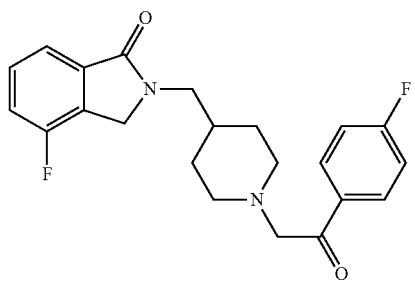

The preparation of the compounds of Formula I from the compounds of Formula II should be within the skill of those trained in the art. Described below are prophetic examples of the preparation of these compounds.

Isolation or purification of the enantiomers/diastereomers of the compounds of the invention may be achieved by conventional methods known in the art, e.g., column purification, preparative thin layer chromatography, preparative HPLC, chiral separation, crystallization, trituration, simulated moving beds and the like.

The Compound of Formula I, wherein R$^1$ is H, and wherein R$^2$ is methyl, and wherein R$^3$ is H, may be prepared by reacting the compound of Formula III with methylmagnesium bromide in a solvent such as tetrahydrofuran or diethyl ether. The reaction may be summarized in the reaction scheme below:

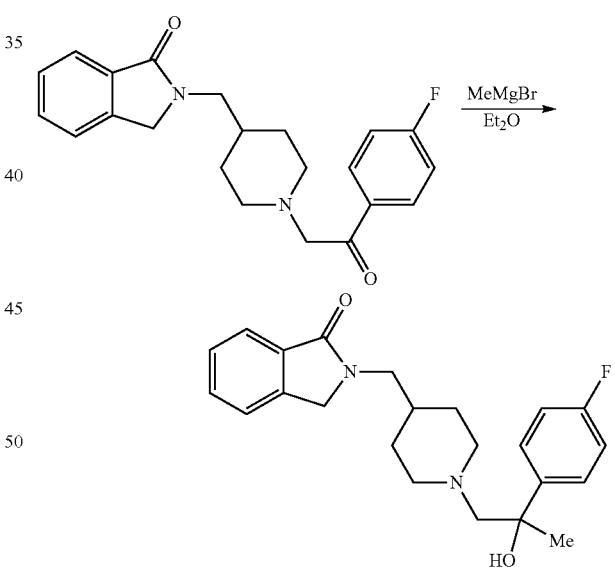

Similar compounds of Formula I wherein R$^2$ is C$_{1-6}$ alkyl (e.g., ethyl, propyl or isopropyl) may be prepared in an analogous manner.

The Compound of Formula I wherein R$^1$ is H, and wherein R$^2$ is methyl, and wherein R$^3$ is —C(O)—R$^4$, and wherein R$^4$ is ethyl, may be prepared by reacting the previously formed compound with propanoyl chloride in a solvent such as dichloromethane, in the presence of a tertiary organic base such as triethylamine. The reaction may be summarized in the reaction scheme below:

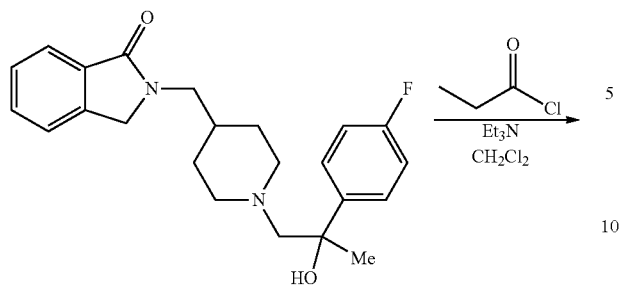

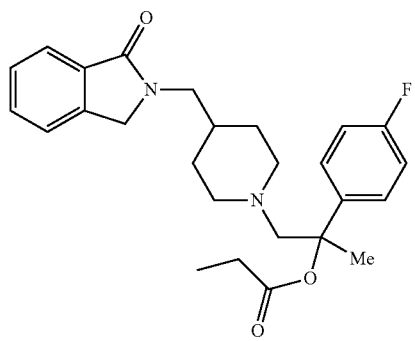

Similar compounds of Formula I wherein R³ is —C(O)—R⁴, and wherein R⁴ is methyl, isopropyl, tert-butyl or other $C_{1-21}$ alkyl may be prepared in an analogous manner.

A Compound of Formula I, wherein R³ is methyl, may be prepared from a corresponding compound wherein R³ is H, by reacting said compound with a strong base such as sodium hydride in an aprotic solvent such as tetrahydrofuran, followed by reacting the resulting sodium alkoxide anion with an alkylating agent such as methyl iodide or methyl sulfate. The reaction may be summarized in the reaction scheme below:

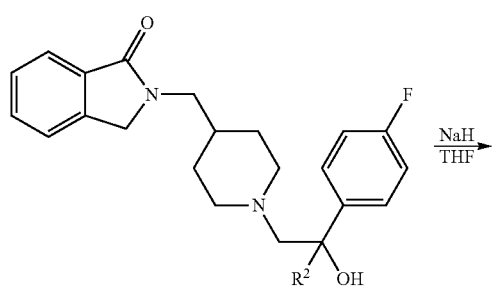

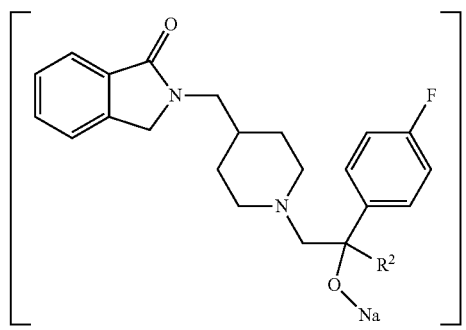

A Compound of Formula I wherein R³ is D, may be prepared from a corresponding compound wherein R³ is H, by reacting said compound with either sodium borodeuteride or lithium aluminum deuteride in an ethereal solvent such as tetrahydrofuran, optionally containing a deuterated protic co-solvent such as methyl alcohol-d ($CH_3OD$). The reaction may be summarized in the reaction scheme below:

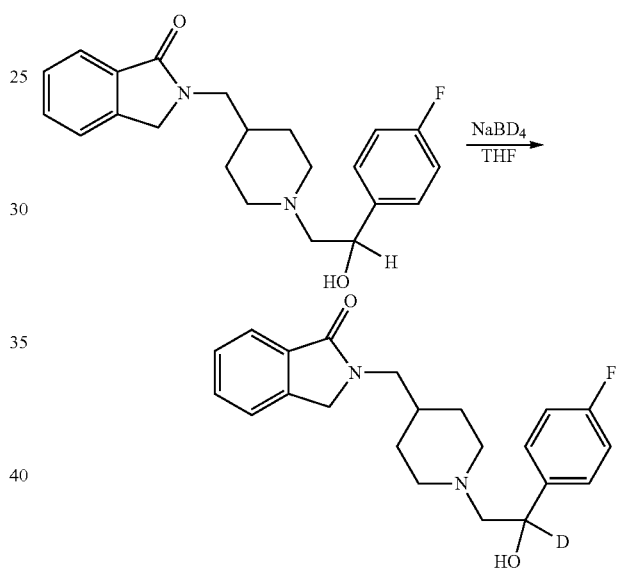

A Compound of Formula I wherein R³ is F, may be prepared from the Compound of Formula III, by reacting said compound with diethylaminosulfur trifluoride (DAST), in a suitable solvent such as dichloromethane, in the presence of benzoyl fluoride. The resulting benzoic ester can then be hydrolyzed under standard conditions, e.g. aqueous sodium hydroxide in tetrahydrofuran, to yield the product wherein R² is H. The reaction may be summarized in the reaction scheme below:

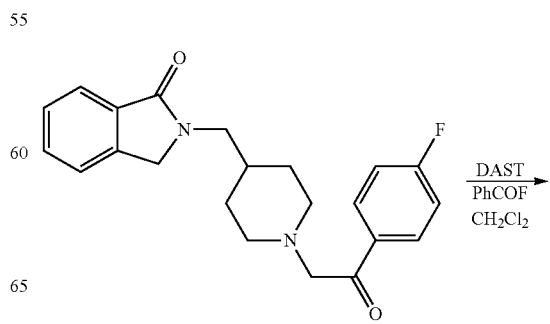

-continued

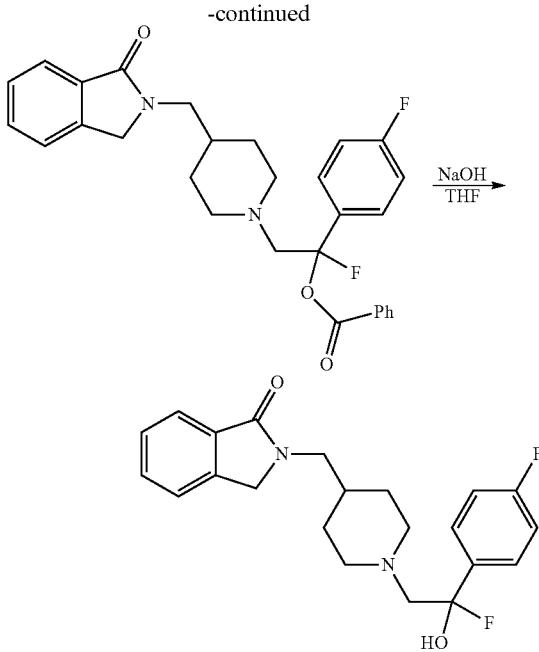

The invention claimed is:

1. A compound of Formula I:

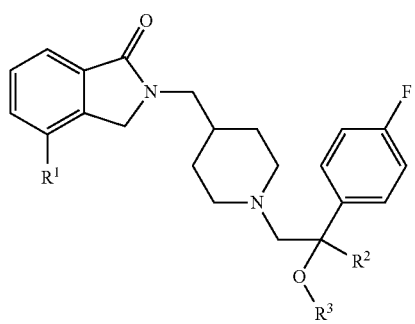

Formula I wherein:
R¹ is H or F;
R² is F, or $C_{1-6}$ alkyl;
R³ is H, $C_{1-6}$ alkyl, or a pharmaceutically acceptable and physiologically labile moiety, wherein, if present, the pharmaceutically acceptable and physiologically labile moiety is —C(O)—R⁴, and wherein R⁴ is $C_{1-21}$ alkyl;
in free form or in the form of a pharmaceutically acceptable salt, hydrate, or solvate thereof.

2. The compound according to claim 1, wherein R¹ is F.
3. The compound according to claim 1, wherein R¹ is H.
4. The compound according to claim 1, wherein R² is $C_{1-6}$ alkyl.
5. The compound according to claim 1, wherein R³ is $C_{1-6}$ alkyl.
6. The compound according to claim 5, wherein R³ is methyl.
7. The compound according to claim 1, wherein R³ is a pharmaceutically acceptable and physiologically labile moiety.
8. The compound according to claim 1, wherein R³ is —C(O)—R⁴, and wherein R⁴ is $C_{1-15}$ alkyl.

9. The compound according to claim 8, wherein R³ is —C(O)—R⁴, and wherein R⁴ is $C_{1-9}$ alkyl.
10. The compound according to claim 9, wherein R³ is —C(O)—R⁴, and wherein R⁴ is methyl, ethyl or propyl.
11. The compound according to claim 10, wherein R³ is —C(O)—R⁴, and wherein R⁴ is methyl.
12. The compound according to claim 1, wherein R³ is H.
13. The compound according to claim 1, wherein the salt is a hydrochloric acid salt.
14. A pharmaceutical composition comprising a compound according to claim 1, in combination or association with a pharmaceutically acceptable diluent or carrier.
15. A method for the treatment or improvement of a psychiatric, central nervous system, gastrointestinal or cardiovascular disease or disorder, comprising administering to a patient in need thereof a compound of claim 1, in free or pharmaceutically acceptable salt form.
16. A method according to claim 15, wherein the disease or disorder is a psychiatric disease or disorder.
17. A method according to claim 15, wherein the disease or disorder is schizophrenia, or the treatment or improvement of one or more of the symptoms of schizophrenia, including any of the negative, positive or general symptoms of schizophrenia.
18. A method according to claim 15, wherein the patient is also receiving treatment with another anti-psychotic agent.
19. A method according to claim 18 wherein the other anti-psychotic agent is selected from olanzapine, clozapine, risperidone, paliperidone, aripiprazole, quetiapine, iloperidone, ziprasidone, asenapine, lurasidone, sertindole, amisulpride, clotiapine, mosapramine, perospirone, sulpiride, zotepine, haloperidol, benperidol, loxapine, molindone, pimozide, thioridazine, mesoridazine, thiothixene, chlorprothixene, fluphenazine, trifluoperazine, chlorpromazine, perphenazine, prochlorperazine, droperidol, and zuclopenthixol.
20. The method according to claim 15, wherein said disease or disorder is selected from a group consisting of obesity, anxiety, depression (for example refractory depression and MDD), psychosis, sleep disorders (particularly sleep disorders associated with schizophrenia and other psychiatric and neurological diseases), sexual disorders, migraine, conditions associated with cephalic pain, social phobias, agitation, agitation in dementia (e.g., agitation in Alzheimer's disease), agitation in autism and related autistic disorders, gastrointestinal disorders such as dysfunction of the gastrointestinal tract motility, post-traumatic stress disorder, or impulse control disorders, intermittent explosive disorder.
21. A method according to claim 15, wherein the disease or disorder is a sleep disorder.
22. A method according to claim 21, wherein the patient is also receiving treatment with another sleep agent.
23. A method according to claim 15, wherein the disease or disorder is selected from anxiety, depression or emotional abnormality, narcotic intoxication, narcotic addiction, sharp pain, dyskinesia, cerebrovascular disease, epilepsy, dementia including Alzheimer's disease, Parkinson's syndrome, brain tumor, attention deficit disorder, irritable bowel syndrome, irritable colon, spastic colon, colitis mucosus, enterocolitis, diverticulitis, dysentery, hypertension, arrhythmia, or angina pectoris.

24. A compound of Formula I:

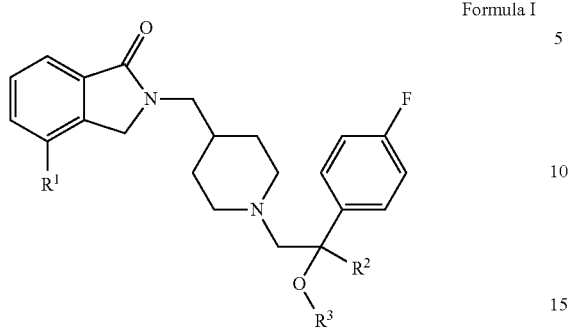

Formula I wherein:
$R^1$ is H or F;
$R^2$ is D;
$R^3$ is $C_{1-6}$ alkyl, or a pharmaceutically acceptable and physiologically labile moiety, wherein, if present, the pharmaceutically acceptable and physiologically labile moiety is —C(O)—$R^4$, and wherein $R^4$ is $C_{1-21}$ alkyl;
in free form or in the form of a pharmaceutically acceptable salt, hydrate, or solvate thereof.

* * * * *